(12) United States Patent
Sikkenga et al.

(10) Patent No.: US 6,255,525 B1
(45) Date of Patent: Jul. 3, 2001

(54) PROCESS FOR PREPARING PURIFIED CARBOXYLIC ACIDS

(75) Inventors: David Lee Sikkenga, Wheaton; M. Michelle Morie-Bebel, Naperville; Stephen V. Hoover, Aurora, all of IL (US)

(73) Assignee: BP Amoco Corporation, Chicago, IL (US)

( * ) Notice: Subject to any disclaimer, the term of this patent is extended or adjusted under 35 U.S.C. 154(b) by 0 days.

(21) Appl. No.: 09/203,018

(22) Filed: Dec. 1, 1998

Related U.S. Application Data
(60) Provisional application No. 60/067,838, filed on Dec. 5, 1997.

(51) Int. Cl.$^7$ .................................. C07C 51/487
(52) U.S. Cl. ................ 562/412; 562/416; 562/409; 562/418; 562/421; 562/485; 562/486; 562/487; 562/494; 562/483
(58) Field of Search .................. 562/416, 487, 562/413, 483, 486

(56) References Cited

U.S. PATENT DOCUMENTS

| | | | |
|---|---|---|---|
| 2,833,816 | 5/1958 | Saffer | 260/524 |
| 3,240,804 | 3/1966 | Knobloch et al. | 260/525 |
| 3,584,039 | 6/1971 | Meyer | 260/525 |
| 3,649,680 | 3/1972 | McNerney | 260/524 M |
| 3,671,578 | 6/1972 | Ogata et al. | 260/515 P |
| 3,781,346 | 12/1973 | Norton | 260/525 |
| 3,870,754 | 3/1975 | Yamashita et al. | 260/524 R |
| 3,888,921 | 6/1975 | Yamamoto et al. | 260/525 |
| 4,345,089 * | 8/1982 | Nagura et al. | 567/77 |
| 4,794,195 | 12/1988 | Hayashi et al. | 562/414 |
| 4,933,491 | 6/1990 | Albertins et al. | 562/416 |
| 4,950,786 | 8/1990 | Sanchez et al. | 562/416 |
| 5,183,933 | 2/1993 | Harper et al. | 562/414 |
| 5,256,817 * | 10/1993 | Sikkenga et al. | 562/487 |
| 5,563,294 | 10/1996 | Holzhauer et al. | 562/483 |

OTHER PUBLICATIONS

Miriam–Webster's Dictionary, 10$^{th}$ ed. pp. 12, 192 and 855, 1998.*

* cited by examiner

*Primary Examiner*—Paul J. Killos
(74) *Attorney, Agent, or Firm*—Scott P. McDonald

(57) ABSTRACT

A process for preparing an aromatic carboxylic acid having improved purity comprising contacting at an elevated temperature and pressure a mixture comprising an impure aromatic carboxylic acid and a solvent in the presence of hydrogen gas with a carbon catalyst which is essentially free of a hydrogenation metal component.

25 Claims, No Drawings

PROCESS FOR PREPARING PURIFIED CARBOXYLIC ACIDS

RELATED APPLICATIONS

This application claims the benefit of U.S. provisional patent application No. 60/067,838, filed Dec. 5, 1997.

FIELD OF THE INVENTION

This invention relates generally to an improved process for preparing purified aromatic carboxylic acids. More particularly, this invention relates to an improved process for preparing purified aromatic carboxylic acids by contacting a crude aromatic carboxylic acid with hydrogen in the presence of a carbon catalyst.

BACKGROUND OF THE INVENTION

Aromatic carboxylic acids such as terephthalic acid, isophthalic acid and 2,6-naphthalenedicarboxylic acid are useful monomers for the preparation of polymeric materials, particularly polyester materials. For example, 2,6-naphthalenedicarboxylic acid can be reacted with ethylene glycol to prepare a high performance polyester, poly (ethylene-2,6-naphthalate) (PEN). Fibers and film manufactured from PEN have improved strength and superior thermal properties relative to other polyester materials. Films made from PEN demonstrate, for example, superior resistance to gas diffusion and particularly to the diffusion of carbon dioxide, oxygen and water vapor. Because of its exceptional properties, PEN is especially suitable for applications such as food and beverage containers, particularly for so-called "hot-fill" food and beverage containers, tire cord, magnetic recording tape and electronic components.

Methods for preparing 2,6-naphthalenedicarboxylic acid include the bromine-promoted, metal-catalyzed, liquid phase oxidation of 2,6-dialkylnaphthalenes. Such processes are disclosed in U.S. Pat. Nos. 3,870,754; 4,950,786; 4,933,491 and 5,183,933. The bromine-promoted, metal-catalyzed, liquid phase oxidation of 2,6-dialkylnaphthalenes, particularly 2,6-dimethylnaphthalene, produces a crude product containing a variety of impurities such as brominated 2,6-naphthalenedicarboxylic acid, 2-formyl-6-naphthoic acid, 2-naphthoic acid, trimellitic acid and other impurities. These impurities, particularly 2-formyl-6-naphthoic acid, are difficult to remove from crude 2,6-naphthalenedicarboxylic acid. Typically, customers desire that the crude 2,6-naphthalenedicarboxylic acid be purified before it is polymerized to form polymeric materials.

Methods for the purification of 2,6-naphthalenedicarboxylic acid are known. In the aforementioned U.S. Pat. No. 4,933,491, for example, 2,6-naphthalenedicarboxylic acid was purified after reacting the 2,6-naphthalenedicarboxylic acid with a lower alkanoic anhydride to produce a component that is soluble in excess alkanoic anhydride. The "solubilized" 2,6-naphthalenedicarboxylic acid was optionally treated with one or more purification procedures. U.S. Pat. No. 3,649,680 to McNarney discloses a process for purifying aromatic carboxylic acids wherein a mixture of water and an alkanol are added to an impure carboxylic acid paste, the carboxylic acid is separated from the alkanol/water mixture, and the purified carboxylic acid is subsequently washed with water. U.S. Pat. No. 3,671,578 to Ogata discloses a process for preparing 2,6-naphthalenedicarboxylic acid wherein the monoalkali salt of 2,6-naphthalenedicarboxylic acid is heated in water or a water-containing organic solvent, causing disproportionation thereof into 2,6-naphthalenedicarboxylic acid and the dialkali salt of 2,6-naphthalenedicarboxylic acid. U.S. Pat. No. 3,888,921 to Yamamoto et al., discloses a process for purifying 2,6-naphthalenedicarboxylic acid wherein an aqueous solution of a dialkali salt of crude 2,6-naphthalenedicarboxylic acid is prepared, then 40 to 97 mole percent of the dialkali salt is precipitated as a monoalkali salt while maintaining the pH of the aqueous solution at a value of not lower than 6.3, and converting the precipitate to 2,6-naphthalenedicarboxylic acid. It is disclosed in the Yamamoto et al. patent that the aqueous solution of the dialkali salt of 2,6-naphthalenedicarboxylic acid can be at a temperature of 60° C.–350° C. in the presence of potassium or sodium hydroxide, and it is disclosed that the solution can be treated with a reducing agent such as hydrogen gas, sodium dithionite, lithium aluminum hydride or sodium borohydride. U.S. Pat. No. 3,781,346 to Norton discloses a process for purifying naphthalene carboxylic acids comprising reacting a solid ammonium salt of the acid with steam at a temperature of from about 200° C. to about 300° C. U.S. Pat. No. 4,794,195 to Hayashi et al. discloses that it is impossible to purify crude naphthalenedicarboxylic acid to a high purity only by crystallization, and that it is necessary to combine the method of crystallization with other methods such as thermal treatment, oxidative treatment or reductive treatment. However, no specific means for conducting such treatments on 2,6-naphthalenedicarboxylic or other naphthalenedicarboxylic acid is disclosed. USSR Inventor's Certificate No. 486,008, to Kulakov et al. published on Jan. 15, 1976, discloses a method for purifying 2,6-naphthalenedicarboxylic acid by treating impure 2,6-naphthalenedicarboxylic acid having a particle size of 0.05–0.35 mm and containing up to 30% naphthalenemonocarboxylic acid with an aliphatic carboxylic acid at 180–250° C. U.S. Pat. No. 5,563,294 to Sikkenga et al., discloses a process for purifying 2,6-naphthalenedicarboxylic acid using hydrogen and a noble metal supported on carbon as a hydrogenation catalyst. U.S. Pat. No. 3,584,039 to Meyer discloses a process for preparing fiber-grade terephthalic acid by catalytic hydrogen treatment of dissolved impure terephthalic acid using a carbon catalyst containing noble metals. The processes described are either complicated or require the use of a potentially expensive noble metal catalyst. What is needed is a simpler process for purifying aromatic carboxylic acids, preferably one that does not require the use of potentially expensive metal catalysts.

SUMMARY OF THE INVENTION

Surprisingly, we have found that aromatic carboxylic acids may be purified by a relatively simple process that does not require the use of potentially expensive catalytic metals.

In our process, an impure aromatic carboxylic acid is purified by treating the impure acid at elevated temperature and pressure in the presence of a solvent, hydrogen gas, and a carbon catalyst which is essentially free or free of added metals such as noble metals. By "essentially free" we mean less than about 0.10 weight percent, preferably less than about 0.07 weight percent and more preferably less than about 0.03 weight percent metal based on the weight of the carbon catalyst. By "free" we mean that no hydrogenation or noble metal has been purposely or intentionally added to the carbon catalyst either before or after its manufacture.

Our invention is particularly suited to purifying naphthalenedicarboxylic acids, most preferably 2,6-naphthalenedicarboxylic acid. The preferred solvent typically is water.

Although it is known that carbon treatment can be used to remove color by adsorption of colored impurities, we have determined that a carbon catalyst essentially free or free of added noble metal hydrogenation components can be used in the presence of hydrogen gas to effectively hydrogenate aldehyde impurities in the crude aromatic carboxylic acid.

For example, 2-formyl-6-naphthoic acid (2-FNA) is an impurity that causes an increase in color of polyester made from 2,6-naphthalenedicarboxylic acid. 2-formyl-6-naphthoic acid in crude or impure 2,6-naphthalenedicarboxylic acid can be hydrogenated to 2-methyl-6-naphthoic acid in accordance with our invention by using a carbon catalyst essentially free of noble metal hydrogenation components. Thus, in addition to removing colored impurities, the process of this invention removes deleterious aldehyde components without the use of expensive noble metal hydrogenation components.

DETAILED DESCRIPTION OF THE INVENTION

In our invention, an aromatic carboxylic acid is contacted with a carbon catalyst in the presence of a solvent at an elevated temperature and pressure in the presence of hydrogen.

Although the aromatic carboxylic acids that can be purified by the process of this invention can be any aromatic carboxylic acid such as terephthalic acid, isophthalic acid, t-butylisophthalic acid, a naphthalenedicarboxylic acid such as a 1,5-, 2,6- or 2,7-naphthalenedicarboxylic acid, and the like, we have found the invention to be particularly suitable for purfiying naphthalenedicarboxylic acids. Our invention therefore will be described in detail using 2,6-naphthalenedicarboxylic acid (2,6-NDA) as the aromatic acid which is purified.

In 2,6-NDA applications, in addition to the removal of 2-FNA, our invention provides for the purification of 2,6-naphthalenedicarboxylic acid without the excessive production of dicarboxytetralins (DCTs). Dicarboxytetralins are formed when one ring of the 2,6-naphthalenedicarboxylic acid molecule is hydrogenated, and the ability to purify 2,6-NDA in the presence of hydrogen while minimizing the formation of DCTs is an additional unexpected benefit.

In this embodiment of our invention, crude 2,6-naphthalenedicarboxylic acid is at least partially dissolved in a suitable solvent, preferably water, at an elevated temperature, and contacted with a carbon catalyst in the presence of hydrogen. During this reaction with hydrogen, certain impurities in the 2,6-naphthalenedicarboxylic acid are reduced.

After this treatment, the mixture is cooled to crystallize the purified 2,6-naphthalenedicarboxylic acid. The purified 2,6-naphthalenedicarboxylic acid is separated from the mother liquor by one or more suitable methods for separating solids from liquids. The purified 2,6-naphthalenedicarboxylic acid optionally are washed with pure solvent to remove any adhering mother liquor.

The 2,6-naphthalenedicarboxylic acid used in the purification process of this invention can be obtained from any source. A preferred source of 2,6-naphthalenedicarboxylic acid, however, is 2,6-naphthalenedicarboxylic acid prepared by the liquid phase, metal-catalyzed oxidation of a 2,6-dialkyl or 2-acyl-6-alkyl naphthalene such as, for example, 2,6-dimethylnaphthalene, 2-methyl-6-acetylnaphthalene, 2-methyl-6-butylnaphthalene, 2,6-diethyl-naphthalene, 2,6-diisopropylnaphthalene, and the like.

Methods for conducting the liquid phase, heavy-metal catalyzed oxidation of an alkyl- or acyl-substituted aromatic compound, such as the naphthalene compounds described hereinabove, to the corresponding aromatic carboxylic acid are well known in the art. For example, U.S. Pat. Nos. 5,185,933; 4,950,786; 4,933,491; 3,870,754; 2,833,816 and U.S. patent application Ser. No. 08/827,039 disclose such oxidation methods. In general, suitable heavy-metal oxidation catalysts include those metals having an atomic number of about 21 to about 82, inclusive. The preferred oxidation solvent is a low molecular weight monocarboxylic acid having 2 to about 6 carbon atoms, inclusive, preferably acetic acid or mixtures of acetic acid and water. A reaction temperature of about 300° F. to about 450° F. is typical, and the reaction pressure is such that the reaction mixture is under liquid phase conditions. A promoter such as a low molecular weight ketone having 2 to about 6 carbon atoms or a low molecular weight aldehyde having 1 to about 6 carbon atoms can also be used. Bromine promoter compounds known in the art such as hydrogen bromide, molecular bromine, sodium bromide and the like can also be used. A source of molecular oxygen is also required, and typically it is air.

A particularly suitable method for oxidizing 2,6-dialkyl and 2-acyl-6-alkylnaphthalenes, and particularly 2,6-dimethylnaphthalene, to 2,6-naphthalenedicarboxylic acid is disclosed in U.S. Pat. No. 4,933,491 to Albertins et al. and in U.S. Pat. No. 5,183,933 to Harper et al., and in U.S. patent application Ser. No. 08/827,039. Suitable solvents for such liquid phase oxidation reaction include benzoic acid, any aliphatic $C_2$–$C_6$ monocarboxylic acid such as acetic acid, propionic acid, n-butyric acid, isobutyric acid, n-valeric acid, trimethylacetic acid, caproic acid, and water. Preferably the solvent is a mixture of water and acetic acid, which mixture is preferably 1 to 20 weight percent water. The source of molecular oxygen employed in such liquid phase oxidation can vary in molecular oxygen content from that of air to oxygen gas. Because of economy, air is the preferred source of molecular oxygen.

The catalyst employed in such oxidation of a 2,6-dialkyl or 2-acyl-6-alkylnaphthalene comprises a bromine-containing compound and at least one of a cobalt- and manganese-containing compound. Preferably, the catalyst comprises cobalt-, manganese-, and bromine-containing components. The ratio of cobalt (calculated as elemental cobalt) in the cobalt component of the catalyst to 2,6-dimethylnaphthalene in the liquid phase oxidation is in the range of about 0.1 to about 100 milligram atoms (mga) per gram mole of 2,6-dimethylnaphthalene. The ratio of manganese (calculated as elemental manganese) in the manganese component of the catalyst to cobalt (calculated as elemental cobalt) in the cobalt component of the catalyst in the liquid-phase oxidation is in the range of from about 0.1 to about 10 mga per mga of cobalt. The ratio of bromine (calculated as elemental bromine) in the bromine component of the catalyst-to-total cobalt and manganese (calculated as elemental cobalt and elemental manganese) in the cobalt and manganese components of the catalyst in the liquid-phase oxidation is in the range of from about 0.1 to about 1.5 mga per mga of total cobalt and manganese. Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromide can be employed. The 0.1:1.0 to 1.5:1.0 bromine-to-total cobalt and manganese milligram atom ratio is provided by a suitable bromine source such as elemental bromine ($Br_2$), or ionic bromide (e.g., HBr, NaBr, KBr, NH$_4$Br, etc.), or organic bromides which are known to provide bromide ions at the operating temperature of the oxidation (e.g., bromobenzenes, benzyl-bromide, tetrabromoethane, ethylenedibromide, etc.). The total bromine in molecular bromine and ionic bromide is used to determine satisfaction of the elemental bromine-to-total cobalt and manganese milligram atom ratio of 0.1:1.0 to 1.5:1.0. The bromine ion released from the organic bromides at the oxidation operating conditions can be readily determined by known analytical means. Tetrabromoethane, for example, at operating temperatures of 335° F. to 440° F. has been found to yield about 3 effective gram atoms of bromine per gram mole.

In operation, the minimum pressure at which the oxidation reactor is maintained is that pressure which will maintain a substantial liquid phase of the 2,6-dialkyl or 2-acyl-6-alkylnaphthalene and at least 70 weight percent of the solvent. The 2,6-dialkyl or 2-acyl-6-alkylnaphthalene and solvent not in the liquid phase because of vaporization is removed from the oxidation reactor as a vapor-gas mixture, condensed, and then returned to the oxidation reactor. When the solvent is an acetic acid-water mixture, suitable reaction gauge pressures in the oxidation reactor are in the range of from about 0 kg/cm$^2$ to about 35 kg/cm$^2$, and typically are in the range of from about 10 kg/cm$^2$ to about 30 kg/cm$^2$. The temperature range within the oxidation reactor is generally from about 250° F., preferably from about 350° F. to about 450° F., preferably to about 420° F. The solvent residence time in the oxidation reactor is generally from about 20 to about 150 minutes and preferably from about 30 to about 120 minutes.

Such oxidation can be performed either in a batch, continuous, or semicontinuous mode. In the batch mode, the naphthalene compound, solvent and the catalyst components are initially introduced batchwise into the reactor, and the temperature and pressure of the reactor contents are then raised to the desired levels for the commencement of the oxidation reaction. Air is introduced continuously into the reactor. After commencement of the oxidation reaction, for example, after all of the 2,6-dialkyl or 2-acyl-6-alkylnaphthalene has been completely introduced into the reactor, the temperature of the reactor contents is raised. In the continuous mode, each of the naphthalene compound, air, solvent, and catalyst are continuously introduced into the reactor, and a product stream comprising 2,6-naphthalenedicarboxylic acid and catalyst components dissolved in the solvent is withdrawn from the reactor. In the semicontinuous mode, the solvent and catalyst are initially introduced into the reactor and then the 2,6-dialkyl or 2-acyl-6-alkylnaphthalene and air are continuously introduced into the reactor. For large-scale commercial operation it is preferable to use a continuous oxidation process. In such a process wherein 2,6-dimethylnaphthalene is oxidized, the weight ratio of monocarboxylic acid solvent to 2,6-dimethylnaphthalene is preferably about 2:1 to about 12:1, the mga ratio of manganese to cobalt is about 5:1 to about 0.3:1, the mga ratio of bromine to the total of cobalt and manganese is about 0.3:1 to about 0.8:1, and the total of cobalt and manganese, calculated as elemental cobalt and elemental manganese is at least about 0.40 weight percent based on the weight of the solvent, and the oxidation reaction temperature is about 370° F. to about 420° F. Acetic acid is the most suitable solvent for such preferred continuous oxidation of 2,6-dimethylnaphthalene.

After an oxidation reaction is completed, the oxidation product mixture can be heated to a high temperature, e.g. 500° F. to 700° F., to reduce undesirable impurities contained in the oxidation reaction mixture.

Subsequent to the oxidation reaction and optional high temperature treatment, the oxidation reaction mixture is typically cooled to promote the crystallization of the 2,6-naphthalenedicarboxylic acid from the reaction mixture; and the 2,6-naphthalenedicarboxylic acid is partitioned (i.e., separated) from the oxidation reaction mixture by any suitable means for separating a solid from a liquid phase. For example, by centrifugation, filtration and the like. The separated 2,6-naphthalenedicarboxylic acid is typically washed with one or more solvents either at ambient or, preferably, an elevated temperature. Most suitably the wash solvent is water, acetic acid or other low molecular weight aliphatic carboxylic acid or mixtures of water and a low molecular weight carboxylic acid. The 2,6-naphthalenedicarboxylic acid isolated from such an oxidation method contains impurities and by-products such as trimellitic acid and, if a bromine compound is used as a promoter during the liquid phase, brominated naphthalene-dicarboxylic acids. Other impurities include 2-formyl-6-naphthoic acid from the incomplete oxidation of the alkyl group and, typically, the metal catalysts used for the liquid-phase oxidation, various color-producing impurities and other unknown components. Such 2,6-naphthalenedicarboxylic acid typically contains up to about 3 wt. % brominated-2,6-naphthalenedicarboxylic acid, up to about 1 wt. % 2-formyl-6-naphthoic acid and up to about 5 wt. % trimellitic acid. The process of this invention can be used to purify such impure 2,6-naphthalenedicarboxylic acid.

Solvents that are suitable for the purification process of this invention, hereinafter referred to as purification solvents, include any solvent that will at least partially dissolve 2,6-naphthalenedicarboxylic acid at an elevated temperature, which solvent does not react with 2,6-naphthalenedicarboxylic acid, and which does not decompose at an elevated temperature used for this process so as to produce impurities. For example, solvents having reactive groups such as amines, alcohols, phenols and thiols are generally not suitable as solvents. Suitable purification solvents, however, include water, low molecular weight carboxylic acids, and mixtures of water and low molecular weight carboxylic acids. Preferably, such low molecular weight carboxylic acids have about 1 to about 8 carbon atoms and are preferably monocarboxylic acids. Preferably, the low molecular weight carboxylic acids are saturated in that they do not contain any carbon-carbon multiple bonds. Examples of suitable low molecular weight carboxylic acids solvents include acetic acid, propionic acid, iso- and n-butyric acid, benzoic acid, fluoro-, bromo-, chloroacetic acid, and the like. The preferred solvent for the process of this invention is water.

In the present process, the amount of solvent, preferably water, used in the purification reaction is an amount sufficient to dissolve, at the reaction temperature, at least a portion of the 2,6-naphthalenedicarboxylic acid to be purified. Preferably, the amount of solvent used is an amount that will dissolve a major portion and more preferably substantially all of the 2,6-naphthalenedicarboxylic acid to be purified. Purification of impure 2,6-naphthalenedicarboxylic acid occurs when at least 10 weight percent, more preferably at least 20 weight percent of the 2,6-naphthalenedicarboxylic acid is in solution under the reaction conditions for the purification process. Most preferably, all of the 2,6-naphthalenedicarboxylic acid is in solution. The weight ratio of solvent to crude 2,6-naphthalenedicarboxylic acid is suitably at least about 1:1, more preferably at least about 2:1, and most preferably at least about 2.5:1; respectively. Typically, the weight ratio of solvent to 2,6-naphthalenedicarboxylic acid is no more than about 25:1, respectively.

The temperature for the purification process of this invention is suitably at least about 500° F., more preferably at least about 550° F., and most preferably about 550° F. to about 650° F. The temperature for the process is preferably no greater than about 700° F. Above 700° F. excessive decomposition of 2,6-naphthalenedicarboxylic acid may occur.

If the solvent selected has a high vapor pressure at the temperature selected for the purification process, it will be necessary to conduct the reaction in a pressure vessel in order to maintain solvent substantially in the liquid state. Consequently, the pressure for the process should be sufficient to maintain liquid phase conditions, and preferably wherein at least about 75 weight percent of the solvent in the reaction mixture is in the liquid state. For example, when water is used as a solvent the pressure for the reaction is up to about 3000 psig, more preferably 2000 psig. Preferably, the pressure is at least about 200 psig.

The carbon catalyst used in this invention is essentially free, and preferably, free of any noble metal components, such as platinum, palladium, rhodium, ruthenium, osmium, iridium, rhenium, or any mixtures thereof. The catalyst also is preferred to be essentially free of any hydrogenation metal. By "hydrogenation metal," we mean free of metals used to promote hydrogenation, including but not limited to, noble metals. Most preferably, the carbon catalyst of this invention is essentially free, and preferably, free of platinum and palladium. By essentially free we mean less than about 0.10 weight percent, preferably less than about 0.07 weight percent and more preferably less than about 0.03 weight percent metal based on the weight of the carbon catalyst. By free we mean that no metal has been purposely or intentionally added to the carbon catalyst either before of after its manufacture. If the carbon catalyst is in a particulate or divided form such as a pellet, powder, extrudate or the like, preferably each such particle of the carbon catalyst in the total carbon catalyst charge or bed is essentially free, and preferably, completely free of any such added component. Carbon catalysts suitable in the process of this invention are any carbon catalysts that will provide for a reduction in the amount of one or more impurities in the crude aromatic carboxylic acid feed in the presence of hydrogen gas when the crude aromatic carboxylic acid at least partially dissolved in a suitable solvent is contacted with the carbon catalyst. Carbon catalysts derived from wood, coconut, and peat are suitable. For example, carbon that can be purchased under the trade names of Norit C, Calgon PCP, and Norit ROX. However, the preferred carbon catalyst useful in the process of this invention is derived from peat.

The amount of carbon catalyst used is an amount that provides for the purification of the aromatic carboxylic acid being purified. For the purification of crude 2,6-naphthalenedicarboxylic acid in a continuous mode of operation, the amount of carbon catalyst is suitably an amount such that there is about 0.1 to about 20 parts by weight of crude 2,6-naphthalenedicarboxylic acid per part by weight of carbon catalyst per hour, preferably, about 0.2 to about 15 parts by weight of crude 2,6-naphthalenedicarboxylic acid per part by weight of carbon catalyst per hour. The catalyst can be in the powdered, granular or extrudate form.

The amount of hydrogen used, typically in the form of hydrogen gas ($H_2$), should be an amount sufficient to provide for the desired purification of 2,6-naphthalenedicarboxylic acid at the reaction conditions selected for the purification reaction. Preferably, conditions should be selected such that the amount of hydrogen dissolved in the solvent used for the purification is an amount such that the mole ratio of hydrogen ($H_2$) to aldehyde, such as 2-formyl-6-naphthoic acid, impurity is about 1 to about 150, more preferably about 2 to about 20.

After the treatment of the reaction mixture with hydrogen in the presence of the carbon catalyst, the reaction mixture is separated from the carbon catalyst. If a continuous process is used wherein the reaction mixture is passed over or through a fixed bed of carbon catalyst, this separation step is not necessary. However, if the carbon catalyst is dispersed in the reaction mixture such as in a batch-type reaction where the carbon catalyst is simply added to the reaction mixture in for example, a granular form, the carbon catalyst must be separated from the reaction mixture by one or more means such as filtration, settling or centrifugation. When the catalyst is used in such dispersed form, it is desirable to use conditions wherein the 2,6-naphthalenedicarboxylic acid is substantially and, more preferably, completely dissolved in the reaction solvent thereby facilitating the separation of the reaction mixture from the carbon catalyst. However, when operating under reaction conditions wherein the 2,6-naphthalenedicarboxylic acid is not all in solution, the carbon catalyst can be contained on one side of a screen or filter or other barrier that permits the passage of dissolved 2,6-naphthalenedicarboxylic acid, dissolved impurities and hydrogen gas.

Following the purification treatment of this invention, the reaction product mixture is subject to a separation process wherein the solid, purified 2,6-naphthalenedicarboxylic acid formed is separated from the solvent used. Any means for separating a solid from a liquid is suitable for this separation step. For example, filtration (vacuum, atmospheric, or at elevated pressures) settling and centrifugation can be employed. Combinations of these separation procedures can also be used.

It is also preferable to wash the purified 2,6-naphthalenedicarboxylic acid with a solvent after it is separated from the solvent used for the high temperature process. This washing step further purifies the 2,6-naphthalenedicarboxylic acid by removing residual solvent used for the purification process. The residual solvent typically contains undesirable impurities. Most preferably, the solvent used to wash the 2,6-naphthalenedicarboxylic acid is the same solvent used for the purification treatment. The amount of solvent used to wash the 2,6-naphthalenedicarboxylic acid is an amount sufficient to remove at least a major portion of the solvent remaining from the purification process. Preferably, the weight ratio of wash solvent to 2,6-naphthalenedicarboxylic acid is at least about 0.2:1, more preferably at least about 0.4:1, and most preferably at least about 0.8:1, respectively. The washing can be completed in any suitable manner; however, it is preferable to simply add the washing solvent to the 2,6-naphthalenedicarboxylic acid while the 2,6-naphthalenedicarboxylic acid is still in the apparatus used to separate the 2,6-naphthalenedicarboxylic acid from the reaction mixture solvent. For example, when a centrifuge is used to separate the 2,6-naphthalenedicarboxylic acid from the reaction mixture solvent, washing can be completed by adding the washing solvent to the centrifuge cake while the cake is still on the centrifuge basket. Alternatively, the 2,6-naphthalenedicarboxylic acid can be washed by slurrying the 2,6-naphthalenedicarboxylic acid in the wash solvent followed by a second separation step wherein the wash solvent is separated from the 2,6-naphthalenedicarboxylic acid. Two or more washing steps can be used. Most preferably, the washing solvent should be at an elevated temperature, for example, a temperature from about 200° F. to about 500° F., preferably at a temperature of 300° F. to about 450° F.

Prior to separating the purified 2,6-naphthalenedicarboxylic acid from the reaction mixture formed in the purification process, the reaction mixture can be cooled to promote crystallization of the 2,6-naphthalenedicarboxylic acid. However, as expected, cooling will cause not only the crystallization of the desired 2,6-naphthalenedicarboxylic acid but will also cause the precipitation or crystallization of undesired impurities. Consequently, a suitable temperature for separating the 2,6-naphthalene dicarboxylic acid from the reaction mixture solvent is a temperature that provides the desired purity of 2,6-naphthalenedicarboxylic acid and the desired recovery of 2,6-naphthalenedicarboxylic acid. For example, the reaction mixture can be cooled to a temperature that is about 20° F. to about 400° F., more preferably about 100° F. to about 200° F. below the reaction temperature used for the purification, before the 2,6-naphthalenedicarboxylic acid is separated from the reaction mixture. Typically, the reaction mixture will be cooled to a temperature greater than 250° F. Preferably, the reaction mixture is cooled to a temperature of no less than about 400° F., most preferably no less than about 450° F. before the 2,6-naphthalenedicarboxylic acid is separated therefrom. Additionally, it is desirable to cool the reaction mixture slowly. Slower cooling of the reaction mixture provides for 2,6-naphthalenedicarboxylic acid having a larger average (mean) particle size, and 2,6-naphthalenedicarboxylic acid having a lower percentage of very small particle size 2,6-naphthalenedicarboxylic acid. The large particle size 2,6-naphthalenedicarboxylic acid allows for a more efficient separation process when 2,6-naphthalenedicarboxylic acid is separated from the reaction mixture solvent because the larger particles do not plug or "blind" filter plates or centrifuge baskets when filtration and/or centrifugation is used for the separation process. The rate of cooling the reaction mixture is preferably no greater than about 50° F. per minute, more preferably no more than about 40° F. per minute, and most preferably no more than about 10° F. per minute. When operating this process in a continuous mode, a scraped-surface tubular heat exchanger can be used to obtain low cooling rates. By using the purification process of this invention, 2,6-naphthalenedicarboxylic acid having a mean particle size, as measured by a Microtrac™ particle analyzer, of at least 50 microns can be obtained. Additionally, the process of this invention can be used to make 2,6-naphthalenedicarboxylic acid having very low levels of fines, for example, less than 5 weight percent of the 2,6-naphthalenedicarboxylic acid is of a particle size less than 11 microns, preferably less than about 2 weight percent.

Even though it is desirable to cool the purification reaction mixture slowly in order to form 2,6-naphthalenedicarboxylic acid with a large particle size and low level of fine particles, it may be advantageous, for example, for economic reasons, to cool the reaction mixture rapidly even though such a procedure produces smaller particle size 2,6-naphthalenedicarboxylic acid and a larger amount of fines. However, we have determined that if such a mixture is again heated in the presence of a solvent, such as water, the original mother liquor, or the original mother liquor with added solvent to an elevated temperature, such as above about 450° F., large particle size 2,6-naphthalenedicarboxylic acid containing low levels of fine particle size 2,6-naphthalenedicarboxylic acid is again formed which can be easily separated from the mother liquor by conventional separation techniques and equipment as described hereinabove.

While not wishing to be bound by theory, it is believed that our process works in part by converting one or more undesired components of the aromatic oxidation reaction mixture into species that are more easily separated from the desired aromatic acid in solid liquid separation steps without converting substantial quantities of the desired acid product into an undesired species.

Thus, in another embodiment of the invention, a process for manufacturing relatively pure aromatic acids from alkyl- or acyl-substituted aromatic compounds can include a first step of oxidizing an alkyl- or acyl-substituted aromatic compound to form a reaction mixture containing impure aromatic acids of the alkyl or acyl-substituted aromatic compound. This reaction mixture includes at least one or more undesired aromatic compound that will exhibit improved separation from a desired aromatic acid in a solid-liquid separation process by hydrogenating a functional group present on the undesired compound. Functional groups particular susceptible to conversion to more easily separated materials include aldehydes, bromides, ketones and alcohols. Aromatic acids and other impurities from the oxidation step are then reacted at an elevated temperature and pressure in a purification solvent in the presence of hydrogen and a carbon catalyst which is essentially free of an added hydrogenation metal component to yield a purified reaction mixture. A solid liquid separation is then performed on the purified reaction mixture to recover purified aromatic acid.

The foregoing process is particularly useful where the oxidation step is conducted in the presence of bromine and one or more catalyst metals selected from the group consisting of cobalt, manganese, and mixtures thereof, where the catalyst comprises peat carbon, or where hydrogen is in an amount of 2 to 20 moles of hydrogen per mole of functional group to be hydrogenated.

The foregoing process is particularly well-suited for the manufacture 2,6-naphthalenedicarboxylic acid where an undesired compound is 2-formyl-6-napthoic acid, and has been shown to improve purity of the 2,6-NDA product without producing increased amounts of dicarboxytetralin in the purified product.

The following examples demonstrate the processes of our invention. In these examples, 2,6-naphthalenedicarboxylic acid is NDA, 2-naphthoic acid is 2-NA, 2-formyl-6-naphthoic acid is FNA, bromo-2,6-naphthalenedicarboxylic acids are Br-NDA, trimellitic acid is TMLA, terephthalic acid is TA, isophthalic acid is IA, 2-methyl-6-naphthoic is 2-Me-6-NA acid, and dicarboxytetralin is DCT. 2,6-Naphthalenedicarboxylic acid used for these examples was prepared by the liquid phase oxidation of 2,6-dimethylnaphthalene using cobalt, manganese and bromine as the oxidation catalyst. The organic components were analyzed by liquid chromatography (LC); the metal analyses were conducted by Inductively Coupled Plasma (ICP) analysis or by x-ray fluorescence spectroscopy (XRF). Bromine was also quantified by XRF. ND or values reported as 0.00 means "not detected."

The color of the 2,6-naphthalenedicarboxylic acid was also evaluated by Tri-stimulus Color measurements, L, a* and b*. The measurement of the b*-value of a solid on the Hunter Color Scale is described in Hunter, *The Measurement* of Appearance, Chapter 8, pp. 102–132, John Wiley & Sons, N.Y., N.Y. (1975), and in Wyszecki et al., Color Science, Concepts and Methods, Quantitative Data and Formulae, 2d Ed., pp. 166–168, John Wiley & Sons, N.Y., N.Y. (1982).

More specifically, the b*-value of purified 2,6-naphthalenedicarboxylic acid was determined using a Diano Match Scan Spectrophotometer as follows. 2,6-Naphthalenedicarboxylic acid was pressed into a pellet by placing 0.5 grams of 2,6-naphthalenedicarboxylic acid into a 13 mm mold and applying 4000 psi pressure for at least 90 seconds. The pellet was then irradiated with white light that was UV-filtered. The spectrum of the visible light reflected from the sample was determined and Tri-stimulus values (X, Y, and Z) were computed using the CIE Standard Observer functions. Using the weight-ordinate method, Tri-stimulus values are obtained from the following equations:

$$X = \sum_{400}^{700} R_l \bar{x}_l,$$

$$Y = \sum_{400}^{700} R_l \bar{y}_l,$$

$$Z = \sum_{400}^{700} R_l \bar{z}_l,$$

where $R_l$ is the percent reflectance of the object at wavelength l and $\bar{x}_l$, and $\bar{y}_l$, and $\bar{z}_l$ are the Standard Observer functions at wavelength l for CIE Illuminant D65. The Tri-stimulus values, X, Y and Z, identify the color of the object in terms of the mixture of the primary lights that match it visually. Tri-stimulus values, however, are of limited use as color specifications because they do not correlate with visually meaningful attributes of color appearance and are not uniform in the spacing of colors as related to visual differences. As a result, "Uniform Color Scales" (UCS) have been adopted which use simple equations to approximate visual response. The UCS scale used by the Diano instrument is the CIE 1976 L*a*b* formula which converts Tri-stimulus values to L*, a*, and b* values as shown below:

$$L^* = 25(100Y/Y_o)^{1/3} - 16$$

$$a^* = 500[(X/X_o)^{1/3} - (Y/Y_o)^{1/3}]$$

$$b^* = 200[(Y/Y_o)^{1/3} - (Z/Z_o)^{1/3}]$$

The L*-value is a measure of the luminosity or whiteness of an object where L*=100 is pure white, L*=0 is black, and in between is gray. The L*-value is strictly a function of the Tri-stimulus Y-value. The b*-value is a measure of the yellowness-blueness attribute where positive b*-values represent yellow appearance and negative b*-values represent blue appearance. The b*-value is a function of both Tri-stimulus values Y and Z. Delta E values are the square root of the sum of the squares of the differences between white and the measured L*, a* and b* values as calculated by the following formula:

$$\text{Delta } E = \sqrt{(100-L^*)^2 + (a^*)^2 + (b^*)^2}$$

Lower Delta E values indicate better overall color.

EXAMPLES 1–5

Examples 1 and 2, and comparison Example 5, were conducted using a continuous flow reaction system consisting of a slurry feed system, a high-pressure hydrogen ($H_2$) addition system, a titanium preheater, two 75 ml titanium reactors (1"ID×6") and a 5 gallon high-pressure 316 stainless steel receiver. Examples 3 and 4 were conducted in a 20 liter high-pressure 316 stainless steel batch reactor fitted with a stirrer and a titanium mesh catalyst basket positioned near the bottom of the reactor. The composition of the crude 2,6-naphthalenedicarboxylic acid feed is shown in Table 1. The crude 2,6-naphthalenedicarboxylic acid was added to the reactors as a 14% by weight slurry of the crude 2,6-naphthalenedicarboxylic acid in water. The carbon catalyst used for Examples 1–5 was, unless otherwise noted, peat carbon in the form of 0.8 mm extrudates supplied by American Norit Company. Example 5 is presented in which the catalyst contained 19.8 g of 0.5% Pd on coconut carbon and 27.4 g of peat carbon. The Pd on carbon catalyst was pre-aged by operation for 93 hours with crude 2,6 NDA. The reactor was then charged with a dual reactor bed containing the aged Pd/carbon in the top bed and fresh peat carbon in the bottom bed. This dual catalyst bed was operated with crude NDA for 85 hours before the sample was taken. This treatment allows a comparison of aged Pd on carbon to the aged peat carbon in Example 2. The product was filtered from the reaction mixture at 440° F. then washed twice with water at 400° F. The amount of water for each wash was 1.5 times the weight of the 2,6-naphthalenedicarboxylic acid. The data from these purification reactions is shown in Table 1.

Example 1 using only pure carbon as catalyst yielded, after 19 hours on stream, a NDA product with a color delta E of 5.6, 0.2% DCT, and 0.006% FNA. The run was continued under various conditions, and a sample taken after 154 hours on stream (Example 2) yielded NDA with a delta E of 8.2, 0.06% DCT, and 0.003% FNA. The conversion values in Table 1 were calculated based on analyses of both the dry product and the mother liquor and indicate that essentially no decrease in FNA conversion occurred over this time on stream.

Comparison Example 5, which utilized both a Pd on carbon (coconut carbon) catalyst and peat carbon produced a product with slightly worse color and almost 10 times more FNA at similar conditions to the carbon only catalyst. This indicates that replacement of the Pd on coconut carbon catalyst with peat carbon catalyst containing no noble metal improved the overall product quality.

Examples 3 and 4 illustrate that starting with a feedstock with a delta E of 22, a product with a delta E of from 11 to 14.9 was obtained while converting 89–72% of the FNA and yielding less than 0.1% of the DCT by-product. It is unexpected that the FNA conversion would be so high with only 30% of the NDA dissolved since it is thought that the FNA is co-crystallized with the NDA and thus not accessible for reaction unless the NDA is dissolved. However, it appears that the dynamics of the system allow almost all of the FNA access to the catalyst and hydrogen so that high FNA conversion occurs.

TABLE 1

| | | Example | | | | |
|---|---|---|---|---|---|---|
| | Feed | 1 | 2 | 3 | 4 | 5 |
| Reaction Mode | | Continuous | Continuous | Batch | Batch | Continuous |
| Run Time (hours)[a] | | 5.5 | 7.0 | 2.00 | 7.00 | 9.5 |
| Catalyst | | 54.70 | 54.70 | 49.0 | 49.00 | 19.8 |

TABLE 1-continued

|  | Feed | Example 1 | Example 2 | Example 3 | Example 4 | Example 5 |
|---|---|---|---|---|---|---|
| Weight (grams) |  |  |  |  |  | Pd-on-Carbon 27.4 Peat Carbon |
| Reaction Conditions |  |  |  |  |  |  |
| Average reactor temperature (° F.) |  | 600 | 600 | 530 | 530 | 600 |
| Receiver pressure (psig) |  | 1730 | 1730 | 1100 | 1100 | 1730 |
| Receiver temperature |  | 510 | 500 | 530 | 530 | 500 |
| Slurry feed rate (grams/minute) |  | 10.0 | 10.1 | NA | NA | 10.0 |
| Hydrogen feed rate (ml/minute at atmospheric pressure and room temperature) |  | 8.0 | 8.0 | NA | NA | 8.0 |
| Total weight NDA processed (grams) |  | 1418 | 14062 | 3876 | 8312 | 14665/7063 |
| Total hours on stream (hours)[b] |  | 19 | 154 | 17 | 52 | 178/85 |
| grams NDA/grams catalyst/hour |  | 1.6 | 1.6 | 5.7 | 1.6 | 4.2/3.1 |
| Dry Product Analysis |  |  |  |  |  |  |
| Colors |  |  |  |  |  |  |
| L* | 89.6 | 96.9 | 96.8 | 92.1 | 90.7 | 94.5 |
| a* | −1.4 | −1.4 | −2.5 | −1.7 | −1.3 | −2.6 |
| b* | 19.6 | 4.4 | 7.2 | 7.5 | 11.6 | 7.1 |
| Delta E | 22.2 | 5.6 | 8.2 | 11.0 | 14.9 | 9.3 |
| Inorganic impurities (ppm wt.) |  |  |  |  |  |  |
| Bromine | 960 | 5.0 |  | 15.0 | 19.0 | 2.0 |
| Cobalt | 495 | 5.0 | 2.6 | <1.0 | 5.0 | 2.0 |
| Manganese | 2135 | 18.0 | 16.7 | 0.8 | 25.8 | 20.0 |
| Iron | 6 | 18.0 | 2.7 | 2.0 | 4.8 | 3.9 |
| Organic components by LC (wt. %) |  |  |  |  |  |  |
| TMLA | 0.975 | 0.0 | 0.0 | 0.0 | 0.0 | 0.0 |
| TA | 0.0 | 0.0 | 0.0 | 0.0 | 0.0 | 0.0 |
| IA | 0.0 | 0.0 | 0.0 | 0.0 | 0.0 | 0.0 |
| DCT | 0.0 | 0.213 | 0.06 | 0.095 | 0.044 | 0.044 |
| NDA | 97.612 | 99.728 | 99.886 | 99.865 | 99.901 | 99.847 |
| Br-NDA | 0.123 | 0.0 | 0.0 | 0.0 | 0.0 | 0.0 |
| FNA | 0.262 | 0.006 | 0.003 | 0.019 | 0.038 | 0.028 |
| 2-NA | 0.052 | 0.0 | 0.0 | 0.0 | 0.0 | 0.0 |
| 2-Me-6-NA | 0.000 | 0.032 | 0.016 | 0.006 | 0.0 | 0.0 |
| Other | 0.977 | 0.021 | 0.035 | 0.016 | 0.017 | 0.082 |
| Total | 100.00 | 100.00 | 100.00 | 100.00 | 100.00 | 100.00 |
| % Conversion based on total product |  |  |  |  |  |  |
| TMLA |  | 75.4 | 74.8 | 59.3 | 94.6 | 100.0 |
| Br-NDA |  | 100.0 | 88.4 | 100.0 | 100.0 | 98.9 |
| FNA |  | 96.3 | 95.4 | 89.1 | 72.1 | 82.4 |
| Wt. % Impurities in total product before filtration |  |  |  |  |  |  |
| DCT | 0.00 | 0.67 | 0.42 | 0.64 | 0.52 | 0.36 |
| 2-NA | 0.05 | 0.32 | 0.38 | 0.11 | 0.22 | 0.33 |
| 2-Me-6-Na | 0.00 | 0.20 | 0.28 | 0.15 | 0.19 | 0.18 |

[a]For continuous runs this is the sampling time
[b]For batch runs, this is the total time catalyst was used

EXAMPLES 6 AND 7

For Example 6, a titanium reactor (350 ml capacity) was charged with 130 g of Norit American Peat Carbon and operated in an up-flow mode with hydrogen gas added to the feed stream. A fluidized sand bath was used to provide heating of the reactor (600° F.). A high pressure pump was used to continuously feed a slurry of 10% crude NDA in water to the reactor. A down-stream receiver vessel was pressurized at 1730 psig to provide the system pressure. The data for Example 6 was obtained on a carbon that had been on-stream long enough to treat 210 g of crude NDA per gram of carbon. Following about 8 hours of continuous feeding of the reactor, the total product that had been collected at about 500° F. was cooled to 440° F. and allowed to settle for 6 minutes. The mother liquor was mostly removed by decanting, and two washes were made by addition of fresh water, reslurry of the NDA at 400° F., settling, and decanting of the mother liquor. The wet purified NDA and the decanted liquid were collected, sampled, dried, weighed, and analyzed to provide the information in Table 2. The dry NDA represents the bulk of the product. Conversions were calculated by comparing the feedstock analysis with the "total product" calculated from the weights and analyses of the NDA and solids from evaporated mother liquor solids.

These results obtained with a 10% slurry (preferred ranged of 5–17% solids) indicate that a purified NDA with only a 30 ppm FNA, less than 3 ppm total Co and Mn, and no detectable BrNDA, TMLA, or DCT was obtained at these conditions with this aged carbon. In addition, the color L* increased from 82.6 in the feed to 95.1 in the product (100 is the best possible L*). These preferred conditions also yielded 92% overall FNA conversion, but less than 1% yield loss due to ring hydrogenation (only 180 ppm dicarboxytetralin) and decarboxylation (0.64% loss of NDA to 2-naphthoic acid).

For Example 7, the same apparatus described above for Example 6 was used, but no carbon was present in the reactor. The feedstock was a 5% slurry of the same crude NDA. The feed flow was 1.7 times higher but the hydrogen gas flow rate was 42 times higher to maximize the potential for hydrogenation without carbon present. In spite of these extreme measures, the results indicate that no FNA conversion occurred and there was no evidence of ring hydrogenation. These results indicate that the carbon is essential for the hydrogenation to occur. In addition, in spite of the low solids concentration and the high loss of NDA to the mother liquor (19.1% compared to 10.9% for Example 6) the product L* was not improved over the feedstock, and the product b* was only slightly improved.

Several of the water-soluble impurities were removed from the crude NDA with 99.8% purity. However, the 310 ppm of FNA in the product is undesirable due to the formation of colored impurities during polymer processing.

TABLE 2

|  | Feedstock | Example 6 | Example 7 |
|---|---|---|---|
| Reaction Conditions | | | |
| Catalyst | NA | Carbon | No Carbon |
| Slurry feed rate (gram/minute) | | 9.0 | 15 |
| Hydrogen feed rate (ml/minute at atmospheric pressure and room temperature) | | 0.6 | 25 |
| Product Separation | | | |
| Mother liquor decant temperature (° F.) | | 440 | 440 |
| 1st, 2nd, Wash decant temperature (° F.) | | 400 | 400 |
| % Original mother remaining after 3rd decant | | 2.86 | 2.80 |
| Dry Product Analysis | | | |
| Colors | | | |
| L* | 82.6 | 95.1 | 81.8 |
| a* | 2.7 | −1.1 | 2.2 |
| b* | 24.6 | 5.9 | 19.6 |
| mean product size (microns)[a] | 22 | 54 | NA |
| Inorganic impurities (ppm (wt)) | | | |
| Cobalt | 1070 | 2.0 | 0.9 |
| Manganese | 360 | 0.6 | 0.3 |
| Cake Organic Components by LC (wt %) | | | |
| TMLA | 0.415 | 0.0 | 0.0 |
| DCT | 0.00 | 0.0 | 0.0 |
| NDA | 97.97 | 99.91 | 99.841 |
| Br-NDA | 0.106 | 0.0 | 0.0 |
| FNA | 0.121 | 0.003 | 0.031 |
| 2-NA | 0.077 | 0.0 | 0.0 |
| 2-Me-6-NA | 0.005 | 0.0 | 0.0 |
| Other | 0.846 | 0.082 | 0.128 |
| Total | 100.0 | 100.0 | 100.0 |
| Dry Mother Liquor Analysis by LC (wt %) | | | |
| TMLA | | 0.177 | 0.206 |
| DCT | | 0.163 | 0.0 |
| NDA | | 81.547 | 91.061 |
| Br-NDA | | 0.0 | 0.0 |
| FNA | | 0.064 | 0.587 |
| 2-NA | | 5.917 | 1.845 |
| 2-Me-6-NA | | 1.284 | 0.133 |
| Other | | 8.154 | 5.066 |
| Total | | 99.975 | 101.161 |
| Fraction of Product solids in mother liquor | | 10.9 | 19.1 |
| % Conversion (Based on Total Products) | | | |
| Br NDA | | 100.0 | 100.0 |
| FNA | | 92.0 | [b] |
| (DCT in total product) | | 0.018 | 0.0 |
| (2-NA in total product) | | 0.643 | 0.353 |
| (6-Me-2-NA in total product) | | 0.139 | 0.025 |

[a]Measured using Microtrac ™ particle analyzer
[b]No conversion of FNA detected While the foregoing examples have been specific to naphthalenic acids, those of ordinary skill will realize that the techniques taught herein are applicable to other aromatic acids such as terephthalic acid, isophthalic acid, and t-butylisophthalic acid. The scope of our invention is therefore meant to be limited only by the following claims.

We claim:

1. A process for preparing an aromatic carboxylic acid having improved purity comprising the steps of (a) contacting at an elevated temperature and pressure a mixture comprising an impure aromatic carboxylic acid dissolved in a purification solvent in the presence of hydrogen with a carbon catalyst which is free of a hydrogenation metal component, (b) cooling the mixture to form crystallized aromatic carboxylic acid having a higher purity than the impure aromatic carboxylic acid, and (c) recovering the crystallized aromatic carboxylic acid from the cooled mixture.

2. The process of claim 1 wherein the aromatic carboxylic acid is 2,6-naphthalenedicarboxylic acid.

3. The process of claim 2 wherein the purification solvent comprises water.

4. The process of claim 1 wherein the carbon catalyst comprises peat carbon.

5. The process of claim 1 wherein the hydrogenation metal is a noble metal.

6. The process of claim 5 wherein the noble metal is platinum or palladium.

7. The process of claim 2 wherein the 2,6-naphthalenedicarboxylic acid for purification is prepared by the liquid phase, heavy metal catalyzed oxidation of 2,6-dimethyl naphthalene.

8. The process of claim 3 wherein the temperature is about 500° F. to about 700° F.

9. The process of claim 1 wherein the aromatic carboxylic acid is isophthalic acid.

10. The process of claim 1 wherein the aromatic carboxylic acid is terephthalic acid.

11. A process for preparing 2,6-naphthalenedicarboxylic acid having improved purity comprising (a) contacting at an elevated temperature and pressure a mixture comprising impure 2,6-naphthalenedicarboxylic acid and a purification solvent in the presence of hydrogen gas with a carbon catalyst which is free of an added noble metal component; (b) separating reaction mixture formed in step (a) from the carbon catalyst to form a separated reaction mixture; (c) cooling the separated reaction mixture to form crystallized purified 2,6-naphthalenedicarboxylic acid and mother liquor; and (d) separating crystallized purified 2,6-naphthalenedicarboxylic acid from the mother liquor.

12. The process of claim 11 wherein the purification solvent is water.

13. The process of claim 11 wherein the carbon is peat carbon.

14. The process of claim 12 wherein the elevated temperature is in the range of about 500° F. to about 700° F.

15. The process of claim 12 wherein the crystallized purified 2,6-naphthalenedicarboxylic acid is separated from the mother liquor at a temperature of at least about 400° F.

16. The process of claim 15 wherein the temperature is at least about 450° F.

17. The process of claim 11 conducted in a continuous mode.

18. A process for manufacturing relatively pure aromatic acids from alkyl- or acyl-substituted aromatic compounds comprising the steps of:

oxidizing an alkyl- or acyl-substituted aromatic compound to form a reaction mixture containing impure aromatic acids of the alkyl- acyl-substituted aromatic compound that will exhibit improved separation from a desired aromatic acid in a solid-liquid separation process by hydrogenating a functional group present on the undesired compound:

reacting impure aromatic acids obtained from the oxidizing step at an elevated temperature and pressure in a purification solvent in the presence of hydrogen and a carbon catalyst which is essentially free of an added hydrogenation metal component to yield a purified reaction mixture; and thereafter performing a solid-liquid separation on the purified reaction mixture to recover purified aromatic acid.

19. The process of claim 18 wherein the aromatic carboxylic acid is 2,6-naphthalenedicarboxylic acid and an undesired compound is 2-formyl-6-napthoic acid.

20. The process of claim 18 wherein the oxidation step is conducted in the presence of bromine and one or more catalyst metals selected from the group consisting of cobalt, manganese, and mixtures thereof.

21. The process of claim 18 wherein the carbon catalyst comprises peat carbon.

22. The process of claim 19 wherein the oxidation step is conducted in the presence of bromine and one or more catalyst metals selected from the group consisting of cobalt, manganese, and mixtures thereof.

23. The process of claim 19 wherein the purified acid recovered from the solid liquid separation step contains no greater amount of dicarboxytetralin on a dry molar basis than did the impure acid from the oxidation step if recovered and measured on a dry molar basis.

24. The process of claim 18 wherein hydrogen is added in an amount of 2 to 20 moles of hydrogen per mole of functional group to be hydrogenated.

25. The process of claim 18 wherein the functional group to be hydrogenated is selected from aldehydes, bromides, ketones and aldehydes and mixtures thereof.

* * * * *

UNITED STATES PATENT AND TRADEMARK OFFICE
CERTIFICATE OF CORRECTION

PATENT NO.      : 6,255,525 B1
DATED           : July 3, 2001
INVENTOR(S)     : David Lee Sikkenga, M. Michelle Morie-Bebel and Stephen V. Hoover It is certified that error appears in the above-identified patent and that said Letters Patent is hereby corrected as shown below:

<u>Column 13,</u>
Line 45, reads "2135   18.0   16.7   0.8"
        should read:
    -- 2135   10.0   16.7   0.8 --

Signed and Sealed this

Fourth Day of February, 2003

JAMES E. ROGAN
*Director of the United States Patent and Trademark Office*